United States Patent [19]

McKinney et al.

[11] 4,058,724
[45] Nov. 15, 1977

[54] ION SCATTERING SPECTROMETER WITH TWO ANALYZERS PREFERABLY IN TANDEM

[75] Inventors: James T. McKinney, Stillwater; Robert F. Goff, White Bear Lake, both of Minn.

[73] Assignee: Minnesota Mining and Manufacturing Company, St. Paul, Minn.

[21] Appl. No.: 591,104

[22] Filed: June 27, 1975

[51] Int. Cl.² .................................................. H01J 37/26
[52] U.S. Cl. .................................... 250/309; 250/292; 250/296; 250/307
[58] Field of Search ............... 250/306, 307, 309, 292, 250/296

[56] References Cited

U.S. PATENT DOCUMENTS

| | | | |
|---|---|---|---|
| 3,480,774 | 11/1969 | Smith | 250/309 |
| 3,665,182 | 5/1972 | Goff | 250/309 |
| 3,845,304 | 10/1974 | Tamura | 250/309 |
| 3,859,226 | 1/1975 | Schillalies | 250/309 |

OTHER PUBLICATIONS

"Direct Comparison of Ion Scattering and Secondary Ion Emission as Tools For Analysis of Metal Surfaces," Greendoner et al., Applied Physics, vol. 4, pp. 243–248, 1974.

Primary Examiner—Craig E. Church
Attorney, Agent, or Firm—Cruzan Alexander; Donald M. Sell; William B. Barte

[57] ABSTRACT

Improved apparatus and method for measuring ions scattered from a surface, to thereby determine the mass of atoms at the surface. The apparatus includes two analyzers, preferably an energy analyzer and mass analyzer positioned in tandem. The mass analyzer may be tuned to pass only ions having the same mass as ions in an incident ion beam, and to reject sputtered ions, some of which may have the requisite energy to pass through the energy analyzer under a given set of conditions.

10 Claims, 5 Drawing Figures

ION SCATTERING SPECTROMETER WITH TWO ANALYZERS PREFERABLY IN TANDEM

BACKGROUND OF THE INVENTION

1. Field of the Invention

This invention relates to improved surface analysis techniques wherein information concerning the surface composition is inferred from the decrease in a kinetic parameter, such as energy, associated with ions scattered off the surface.

2. Description of the Prior Art

Various techniques and apparatus for analyzing surfaces by scattering ions from the surfaces are disclosed in U.S. Pat. Nos. 3,480,774, issued to Smith on Nov. 25, 1969, 3,665,182, issued to Goff and Smith on May 23, 1972 and 3,665,185, issued to Goff on May 23, 1972. Such techniques include impinging a primary ion beam on a sample. The energy of the ions scattered at a given angle is thereafter measured and the intensity of a signal associated with the measured scattered ions is plotted as a function of the ratio of energy of the scattered ions to that of the impacting ions (i.e., $E_1/E_o$) to at least semi-quantitatively identify the elemental composition of the bombarded surface. In the techniques disclosed in these patents, signals resulting from the passage of sputtered ions through the energy analyzer have generally been observed and measured, even when neutralization of surface charge buildup is achieved. The presence of the signal generally attributed to sputtered ions decreases the overall signal-to-noise ratio, and obscures the detection of scattered ions having a low ratio of $E_1/E_o$, which low ratios correspond to those ions that have lost a large fraction of their incident energy as a result of being scattered from surface elements of relatively low atomic mass.

The ion scattering spectrometers (ISS) disclosed in the patents referenced hereinabove appear to require the determination of the energy lost by a scattered ion. Assuming that the ions so measured are indeed scattered ions such that the mass thereof is also known, the mass of the target atom from which the primary ion is scattered at 90° with respect to the incident primary ion beam may be inferred from the expression $E_1/E_o = (M_2 - M_1)/(M_2 + M_1)$, where $E_1$ is the energy of the scattered primary ion, $E_o$ is the energy of the primary ion before scattering, $M_1$ is the mass of the primary ion, and $M_2$ is the mass of the target atom.

A similar relationship can be expressed in terms of the decrease in other kinetic parameters such as velocity and momentum associated with ions as a result of scattering. Thus a determination of the necessary information regarding the scattering events may be made by any of a large variety of analyzers, some of which are generally referred to as energy analyzers, while others may be more appropriately viewed as momentum analyzers (magnetic sector analyzers), or velocity analyzers (time-of-flight spectrometers), or velocity analyzers (time-of-flight spectrometers) but all of which determine some kinetic parameter (i.e., energy, momentum or velocity).

It should be noted that the calibration of most of the analyzers discussed hereinabove (with the exception of the time-of-flight analyzer) is dependent on the charge state of the ion being analyzed. In most cases, the ion is assumed to be singly charged. Where this is not the case, the actual mass or kinetic parameters of the ion can be determined by assuming the proper charge.

These analyzers are all limited in that they fail to distinguish between sputtered and scattered ions and must assume that the detected ions are indeed scattered ions, when in fact many of the detected ions are actually sputtered ions which contribute "noise" and background in the resultant spectra.

SUMMARY OF THE INVENTION

In contrast to the ion scattering spectrometers disclosed in the patents referenced hereinabove, the ion scattering spectrometer of the present invention utilizes an additional analyzer such that a mass-sensitive filtering of the scattered ions is accomplished simultaneously with the measurement of a kinetic parameter. According to elementary algebra, two independent variables may be determined by simultaneously solving two independent equations involving the two variables. The mass and the velocity (two independent variables) can be directly measured with appropriate analyzers, or they can be indirectly determined by the measurement of two related parameter such as energy and momentum. The analyzers of the present invention need only be such that when scattered ions are passed through each of the analyzers to thereby satisfy the requirement for simultaneous solutions, both the mass and kinetic parameters of the detected ions are determined. Thus, any two analyzers that are sensitive to any two of the characteristics consisting of the mass and the three kinetic parameters are sufficient.

The ion scattering spectrometer of the present invention is thus similar to the prior art ISS system in that it includes an ion generator for producing a primary ion beam, which beam is directed along a preselected path to impinge upon and be scattered from a surface of the mateial to be analyzed. In all such ISS systems. ions indicative of surface atoms having a given mass are transmitted to means for receiving the transmitted ions and for converting the received ions into an electronic signal characteristic of the surface atoms.

In the present invention, such a spectrometer includes two independent analyzers from which the characteristics consisting of the mass and the three kinetic parameters may be determined. These analyzers are positioned in tandem adjacent to the surface for accepting ions scattered from the surface and for passing the accepted ions therethrough. A predetermined condition is established within the first of the analyzers through which the accepted ions are directed to allow only ions having a first said kinetic parameter to pass therethrough, while another predetermined condition is established within the second of the analyzers through which the accepted ions are directed to allow only ions having a given mass to pass therethrough. The scattered ions that have a given set of said characteristics are passed through both analyzers and are then detected to generate a signal characteristic of surface atoms having a given mass. If both analyzers are of the type (such as those utilizing magnetic or electrostatic sectors) whereby ions having a different said characteristic are spatially separated, they may be placed in tandem; if one of the analyzers is temporal (e.g., time-of-flight), such an analyzer may have a configuration so as to operate on the ions as they traverse the second, spatial analyzer.

In one embodiment, one of the analyzers may comprise a quadrupole type mass analyzer. In another embodiment, a lens may be provided between the two analyzers to collect the scattered ions passing through the first analyzer and to optimize the passage thereof into the second analyzer. Where a quadrupole mass analyzer is used as the second analyzer, it is preferable to bias the quadrupole analyzer and to utilize a retarding lens between that analyzer and the first analyzer.

In one method of using the present invention, one of the analyzers, for example, the second analyzer, is selected to be a mass analyzer, and is adjusted to pass into the detector only such ions as have the same mass as the ions in the incident beam. The detector then generates a signal corresponding to the instantaneous concentration of scattered ions having a given decrease in a kinetic parameter, e.g., a given energy loss. In this manner, those ions having the same energy as a primary ion scattered from the surface but which are actually sputtered therefrom are rejected by the mass analyzer and do not contribute to the resultant spectrum. Scattered ions having low rations of $E_1/E_o$ which were previously undetectable due to the large sputtered ion peak may now be readily resolved.

DESCRIPTION OF THE PREFERRED EMBODIMENTS

Figure 1:
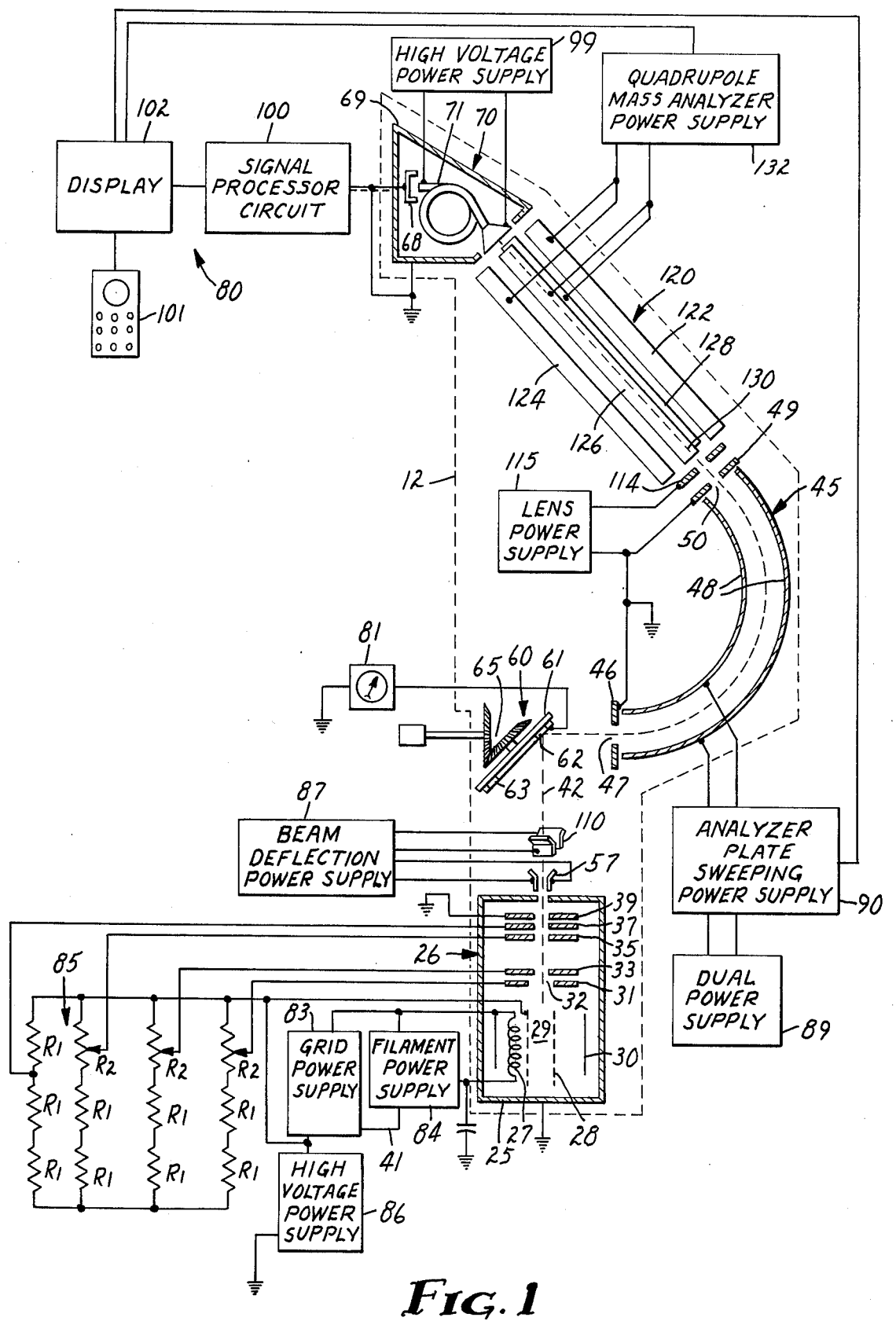
FIG. 1 is a combined cross-sectional view and schematic diagram of the apparatus constructed in accordance with the present invention.
Figure 2:
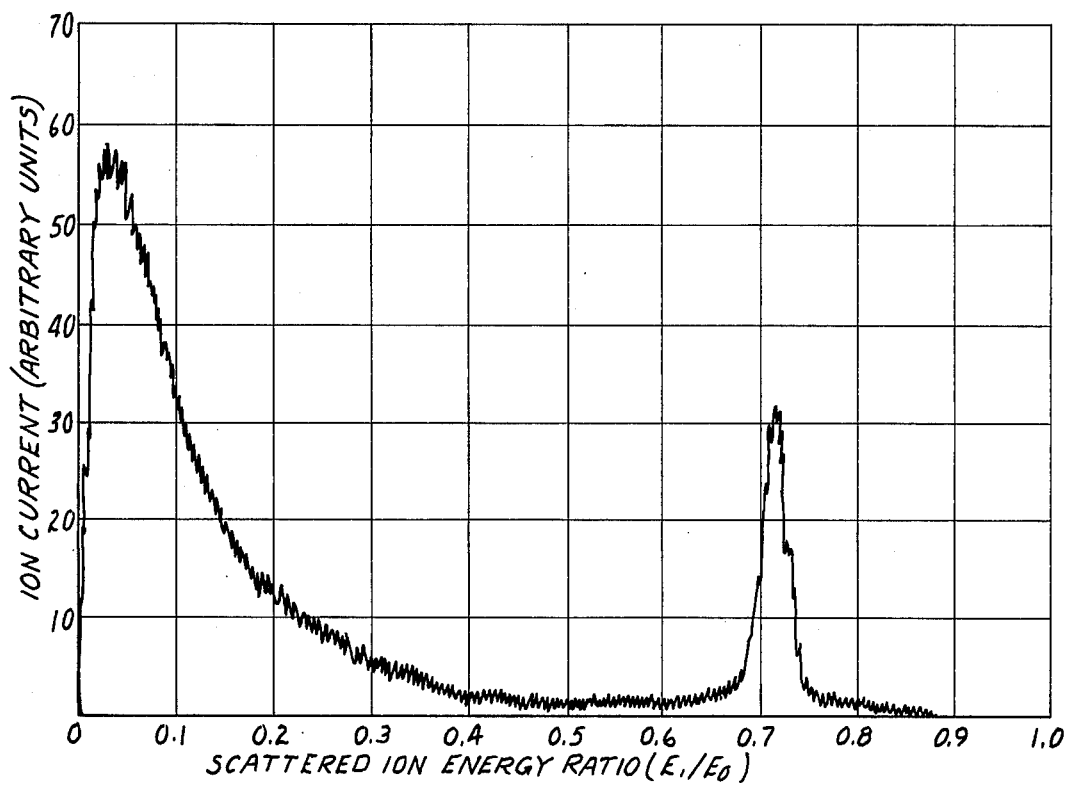
FIGS. 2-5 are graphs of spectra showing the analysis of a tin sample obtained with the present invention.

FIG. 1 is substantially that set forth as FIG. 2 in U.S. Pat. No. 3,665,182, the disclosure of which is incorporated herein by reference, modified to show the present invention.

FIG. 1 shows a compact elemental analyzing apparatus comprising a multipositionable target support 60, an ion generating means 26, beam deflection members 57 and 110, energy analyzer 45, mass analyzer 120, an ion detector 70, and indicating apparatus 80.

In operation, the apparatus described above, with the exception of the indicating apparatus 80, is located within a vacuum chamber 12. A vacuum pump (not shown) is provided to evacuate the chamber to a pressure of less than $10^{-8}$ Torr. A getter and a cryopanel (not shown) are positioned within the chamber to further purify the active elements remaining in the chamber. The pumping off inert gases is discontinued and a gas (or a mixture of gases), such as a noble gas, is released into the chamber until the static pressure is increased to approximately $5 \times 10^{-5}$ Torr. Thereafter, all openings to the chamber are closed. The gas atmosphere within the chamber is utilized to analyze the elements forming the surface of the sample. The noble gas preferably used herein may be any noble gas, however, Helium (He), Neon (Ne) and Argon (Ar) are commonly used. Insulated electrical feedthroughs or connectors provide the necessary electrical connections between the components within the chamer and the electrical apparatus located outside the chamber.

The multiple positionable target support 60 includes a rotatable wheel 61 which contains a number of recessed openings in a lower face thereof to receive samples 62 and 63 which are to be analyzed. The wheel 61 is coupled through the bevel gears shown generally as 65 and through a conventional mechanical feedthrough to a knob positioned outside the vacuum chamber 12. The samples 62 and 63 are held on the face of the wheel 61 by any suitable temporary fastenings such as springs, screws, clips or the like. The target support 60 further includes a sliding contact arm insulated from the supporting members and engagable with indents on the wheel to electrically connect the wheel 61 and the sample being analyzed with a current measuring device 81 for monitoring the level of the ion beam current. Any variety of similar multiple target supports may likewise be provided. Alternatively, larger samples may be mounted singly on a slightly altered sample wheel.

The ion generating means preferably comprises a grounded tubular housing 25, essentially 5.1 × 7.6 × 10.0 cm, adapted to support the operative components of the ion generator. The ion generator, essentially 2.5 × 2.5 × 7.6 cm, includes a heated filament 27 for producing electrons, a highly transparent grid 28 having greater than 80% open area and defining within an extractor plate 31, an ionization region 29, a repeller 30 encircling the filament 27, a first, second, third and fourth anode plates 33, 35, 37 and 39, respectively, and a feedback stabilization loop 41.

A filament power supply 84 powers the filament to produce electrons and a grid power supply 83 biases the grid with respect to the filament 27. The produced electrons from the filament 27 are accelerated by the grid 28 to a potential sufficient to ionize the gas atoms. For example, the electrons would have from 100-125 electron volts of energy, which is sufficient to ionize Helium, which has an ionization potential of about 24 electron volts. The repeller 30 is at the filament potential, and repels or deflects any approaching electrons to result in a long mean-free-path which increases the probability of the electrons striking the atoms of the gas to thereby ionize those atoms.

If the static pressure of the gas within the evacuatable chamber 12 is increased, then the ion beam current is increased. Therefore, by regulating the electron current at a constant gas pressure, the ion beam current is also regulated. The feedback stabilization loop 41 maintains a stable electron current between the filament and the grid and thereby controls the ion beam current throughout pressure changes within the evacuatable chamber 12.

An ion gun voltage divider network 85 biases the extractor plate 31 to a potential to extract positive ions from the ionization region 29. The network 85 includes a number of resistors to selectively bias the extractor plate 31 and the anode plates 33, 35, and 37, except the fourth anode plate 39 which is grounded.

The extractor plate 31 includes an extractor aperture 32 about 0.6 cm diameter, located about the beam axis 42 to extract the positive ions. The ions are focused and apertured by the anode plates forming a primary ion beam. Each anode plate has a potential applied thereto from the network 85. The first anode plate 33 is primarily used to control, modulate and initially focus the extracted ions into a collimated beam. The second anode plate 35, which is spaced from the first plate 33 a distance greater than the spacing between the other plates, is the primary beam collimating and focusing anode. The third anode plate 37 is run at a substantially fixed potential from the voltage divider network 85, while the fourth plate 39 is at ground potential or, alternatively, could be connected to one side of a high voltage power supply 86 and biased with respect to ground. The anode plates are each formed with a small aperture and are constructed of very thin conductive material to control the ion flow and to maintain a monoenergetic beam. The plates are, for example, 0.25 mm thick, in order to minimize the wall surface defining the apertures. In this manner the interaction of the passed ions with the wall surfaces similarly minimizes the attendant loss of energy in the ions passing therethrough.

The beam passing out of the tubular housing 25 is directed through the gas atmosphere toward the sample 62 to be analyzed. Under normal operating conditions, beam perturbing collisions do not cause serious deviations in analysis.

Two pair of deflector plates 57 and 110, positioned near the end of the housing 25 and at opposite sides of the beam axis 42, serve to deflect the beam to enable scanning the beam about a predetermined area of the sample. The plates 57 and 110 are charged by an ion deflector power supply 87 in a conventional manner. The ion beam strikes or bombards the sample 62 on the sample surface about the predetermined area and the impinging primary ions are scattered therefrom. The current to the sample produced by the impinging beam is measured by the current measuring device 81. Such measured current may be used to determine the approximate current density striking the surface of the sample.

The energy analyzer 45 is preferably a conventional 127° electrostatic energy analyzer. The analyzer 45 includes an entrance diaphragm 46 having a rectangular entrance slit 47, an exit diaphragm 49 having a rectangular exit slit 50, and two curved electrostatic analyzer plates 48. The entrance diaphragm 46 and exit diaphragm 49 may be grounded as shown in FIG. 1, or may be charged by a biasing power supply if desired. The slits in the diaphragms have a preferred width of 0.125 mm. The entrance diaphragm 46 is spaced about 1.0 cm from the surface of the sample 62 being analyzed.

The analyzer plates 48 are charged by the output from an analyzer plate sweeping power supply 90 receiving power from a dual power supply 89. The analyzer plate sweeping power supply 90 permits a suitable potential to be applied to the plates 48 to direct ions having a predetermined energy through the slit 50 in the exit diaphragm 49. The analyzer plates 48 have a mean radius of 5.1 cm.

The ions passed through an exit diaphragm 49 are coupled into a mass analyzer 120. The mass analyzer is preferably a quadrupole type mass analyzer having four rods 122, 124, 126 and 128 symmetrically disposed about an axis 130 along which ions pass upon leaving the exit diaphragm 49.

The ions passed from the energy analyzer 45 are preferably coupled to the mass analyzer 120 via an electrostatic lens 114. Such a lens may be energized via power supply 115 to focus the ions passing through the energy analyzer at the entrance region of the quadrupole analyzer 120, thereby optimizing the analysis thereof in the quadrupole mass analyzer 120. Within the mass analyzer 120, a first set of opposing rods 122 and 124 are preferably electrically connected together while the opposing rods 126 and 128 are similarly connected together. Each set of rods is coupled to the quadrupole mass analyzer power supply 132, which produces an rf voltage and a DC bias voltage and which causes appropriate electrostatic fields to be set up along the axis 130 such that a stable trajectory along that axis exists only for ions having a preselected mass. Those ions thus pass along the axis and out of the mass analyzer 120.

The ions passed by both analyzers 45 and 120 are detected and converted by the ion detector 70 into electrons to be received by the electron collector 68. The electron collector 68 converts the collected electrons into an electronic signal.

The ion detector 70 within the enclosure 69 is a continuous channel electron multiplier 71, and is powered by the high voltage power supply 99. The multiplier 71 has a 15 mm entrance cone, which compasses the entire exit area along the axis 130 from the mass analyzer 120. The multiplier may be a commercially available device such as Model No. CM4028 manufactured by Galileo Electro Optics Corp., Galileo Park, Sturbridge, Mass. 01581.

In the present invention, the electronic signal is preferably coupled through a signal processor circuit 100 to extend the duration of pulses associated with discrete scattering events. The processed signal is thereafter coupled to the indicating apparatus 102. The data from the circuit 100 may thus be permanently recorded by the apparatus 102 as a graph or visually indicated on an oscilloscope 101. A signal from the analyzer power supply 90 is similarly coupled to the indicating apparatus 102 so as to enable a spectrum to be displayed which corresponds to a plot of the magnitude of the scattered ions having a given amount of energy loss as a function of the ratio of the energy after scattering to the initial energy of the incident ion beam (i.e., $E_1/E_o$).

Figure 3:
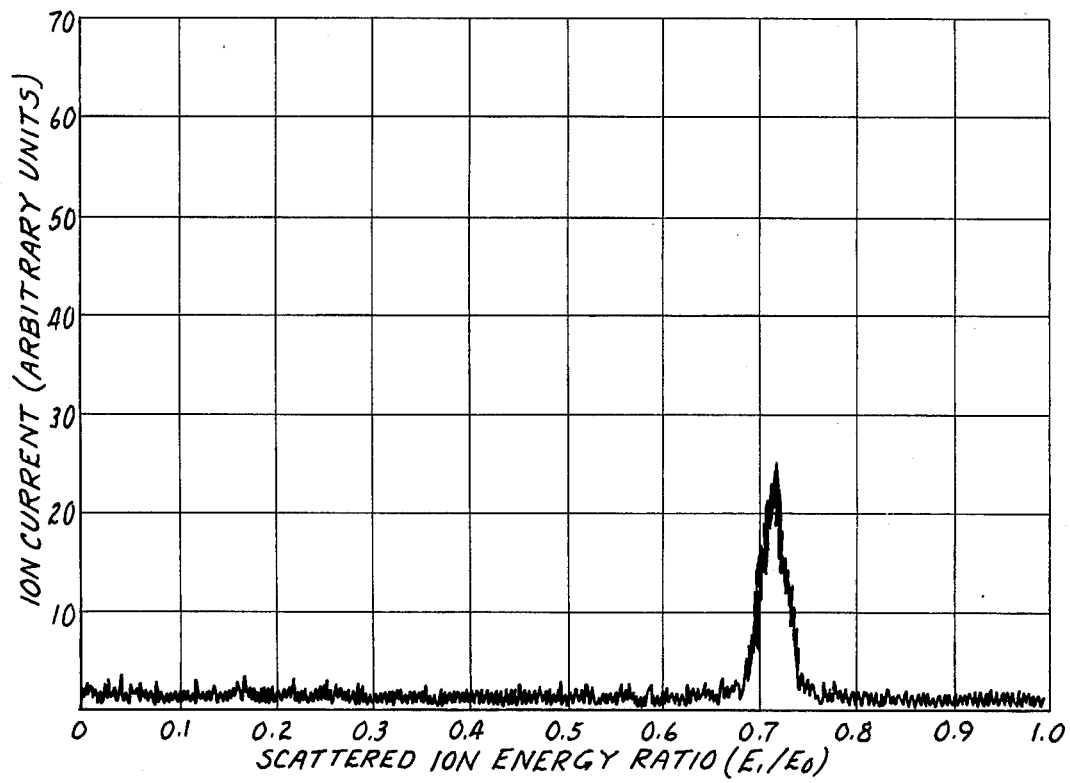

FIGS. 2 and 3 show spectra prepared under substantially the same conditions but in which in one case (i.e., FIG. 3) the mass analyzer 120 has been tuned to reject all ions except those having the same mass as the primary ion beam. During the preparation of these spectra, the chamber 12 was backfilled with a partial pressure of Neon gas and the power supplies associated with the ion generator 26 were energized to produce a primary ion beam of Ne ions having an energy of 1.5 keV. This beam was then directed onto a sample of tin oxide coated on a glass substrate. The ions scattered at 90° were then passed into the energy analyzer 45 and a varying potential applied to the analyzer plates 48 by the analyzer power supply 90 in a conventional manner.

In the preparation of the spectra shown in FIG. 2, the rods 122, 124, 126 and 128, respectively, were all operated at zero potential such that all masses exiting the exit diaphragm 49 were allowed to pass along the trajectory 130 and thereby enter the ion detector 71. In this spectra, the peak at a value of $E_1/E_o$ of approximately 0.7 corresponds to a counting rate of approximately 3100 counts per second. The broad peak extending over an energy ratio range from 0 to approximately 0.4 corresponds to sputtered ions and has a maximum intensity of approximately 5650 counts per second. It may readily be appreciated that signals corresponding to scattered ions having a ratio of $E_1/E_o$ within this range will be appreciably masked by the large sputtered ion signal. Since signals associated with sputtered ions are also present, albeit to a lesser degree, in the higher energy range, such sputtered ion signals will also contribute to a higher noise content in that energy range.

In the preparation of FIG. 3, the same tin sample was bombarded under identical conditions. However, in this case the mass analyzer 120 was energized by the quadrupole analyzer power supply 132 so as to desirably pass only ions having an atomic mass of 20 amu, i.e., to pass only Neon ions. This resulted in a decrease in the total amount of ion current passing through the mass analyzer 120 such that the peak corresponding to Neon ions scattered from the tin surface had relative intensity of approximately 400 counts per second as opposed to the previously observed intensity of 3100 counts per second (see FIG. 2). More significantly, it may be seen that the large peak associated with sputtered ions is entirely eliminated. In this manner, surface contaminants, impurities or the like having a mass corresponding to a scattered ion energy ratio in the range of 0 to 0.4 may now readily be detected.

Figure 4:
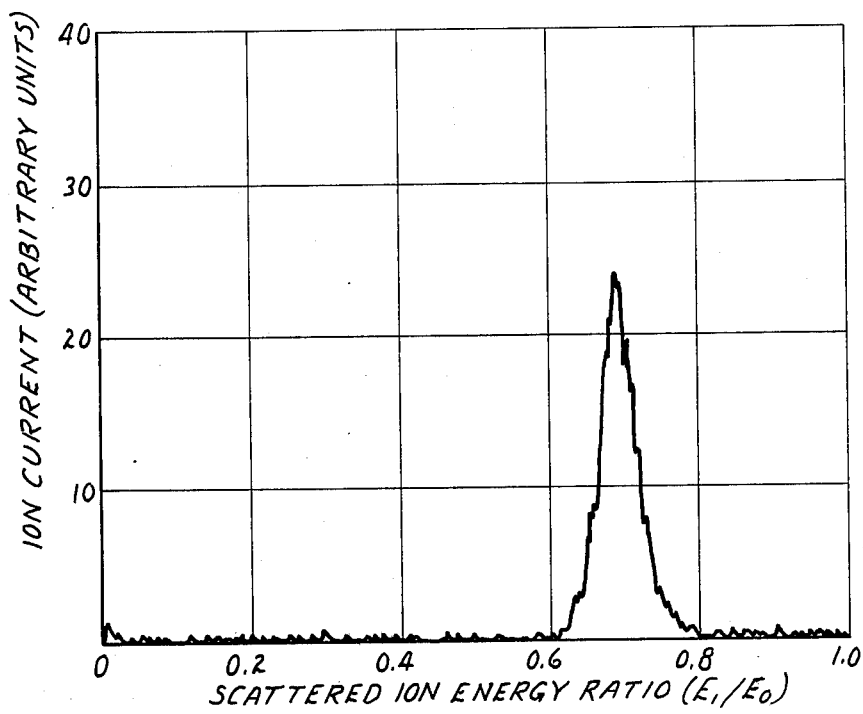
Figure 5:
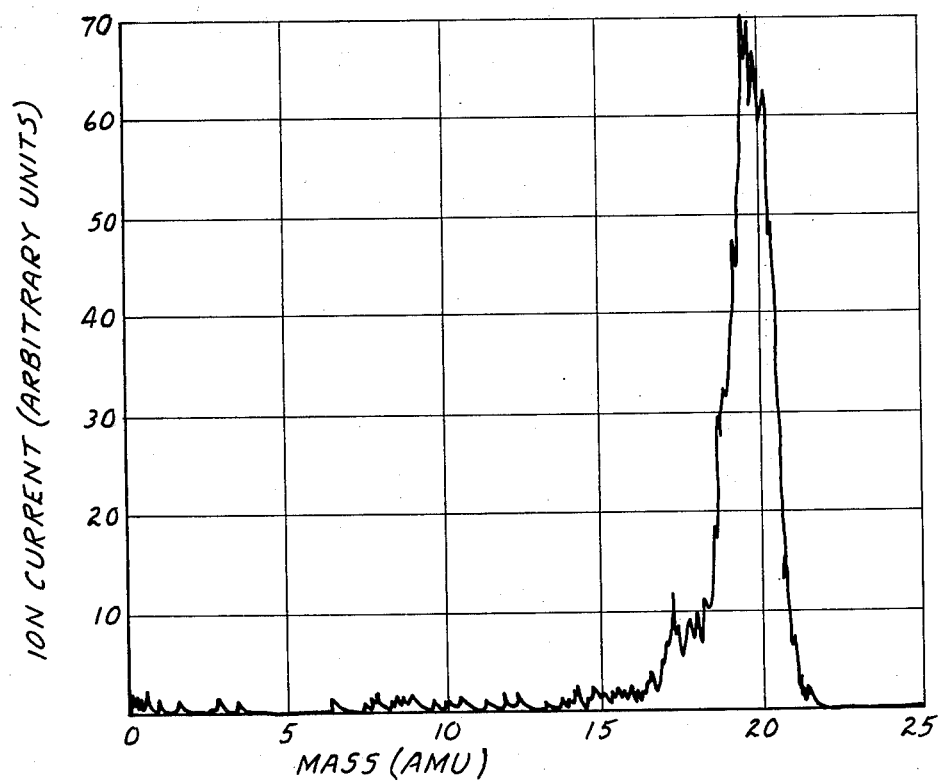

Complete verification of the mass analysis shown in FIGS. 2 and 3 could be possible by showing a series of ISS spectra in which the mass analyzer was tuned to pass different masses. Such verification could also be made by scanning the mass analyzer while holding the energy analyzer fixed at a predetermined value. A pair of such spectra are shown in FIGS. 4 and 5, i.e., an energy analysis at fixed mass and a mass analysis at fixed energy, respectively. The fixed mass in FIG. 4 and the fixed energy in FIG. 5 are those associated with Ne ions (100 eV) elastically scattered from a SnO surface. In the mass analyzed ion scattering spectrum of FIG. 4, the quadrupole mass analyzer is tuned to allow Ne ions (20 amu) to pass therethrough. FIG. 4 is thus substantially the same as that presented in FIG. 3, except that the energy of the bombarding ions was 100 eV rather than 1500 eV.

In preparing the spectrum shown in FIG. 5, the electrostatic energy analyzer was tuned to pass only ions having the appropriate ratio of $E_1/E_o$ corresponding to elastically scattered Ne ions, i.e., 0.7, and the quadrupole mass analyzer was scanned. As may be seen, only ions having a mass of approximately 20 amu were detected, thus indicating proper mass analysis by the guadrupole mass analyzer.

The present invention has additional utility in that the mass analyzer 120 may be tuned to selectively pass other atomic species. Accordingly, while in one embodiment of the present invention, the sputtered ions are prevented from complicating the energy spectra, in another embodiment of the present invention, such sputtered species may be selectively identified. In such an embodiment, the energy analyzer is adjusted to pass a wide spectrum of energies and the mass analyzer is tuned to selectively pass a given mass, thereby enabling the mass analysis of the sputtered ions.

For example, the prior art ion scattering spectrometers have demonstrated, at best, a limited ability to resolve various isotopes of surface elements. With the present invention, such isotopes may be definitively identified by tuning the mass analyzer 120 to pass first one and then another of the isotopes of a given atomic species to determine the relative concentration of each of the isotopes.

Whereas previous ISS systems could not effectively differentiate between most isotopes, the present invention now allows for isotopic separations such as $K^{39}$ and $K^{41}$. The determination of these isotopes on the outer surface of a membrane such as a cell wall is a central factor in the understanding of intercellular communications relating to such cellular phenomena as osmosis and cancerous growth.

Similarly, while the prior art ion scattering spectrometers have been incapable of detecting hydrogen, the analysis of sputtered species may enable such detection. For instance, if excessive oxygen and hydrogen are present on a metallic surface, the combined mass and energy analysis may yield information pertinent to whether the oxygen and hydrogen are due to the increased metallic oxide content or merely absorbed water.

In the past, ion scattering spectrometers have desirably used an isotopically purified probe gas. Such purification is quite costly and thereby the elmination of such a need offers significant savings. With the present invention the mass analyzer 120 may be tuned to reject all ions except those having a mass of a desired isotope of the probe gas, thereby rendering immaterial the presence of other isotopes of the probe gas.

The invention further allows extremely accurate calibration of the energies of scattered ions, inasmuch as a known target may be bombarded with ions of a known isotope and the mass analyzer tuned to accept only ions of that atomic weight. In this manner, the energy analyzer may then be accurately adjusted to pass a maximum scattered signal. With the high signal intensity thus obtained, small variations in the energy of the scattered ions such as may result from chemical bonding effects or variations in the atomic surface topology may be observed.

Having thus described the present invention, what is claimed is:

1. In a method for analyzing the surface of a material comprising
   generating a primary ion beam,
   directing said beam along a preselected path to impinge upon and be scattered from a surface of the material to be analyzed,
   transmitting ions indicative of surface atoms having a given mass, and
   receiving the transmitted ions and converting the received ions into an electronic signal characteristic of said surface atoms,
   the improvement wherein the step of transmitting comprises
   positioning two independent analyzer means in tandem adjacent to said surface for determining a kinetic parameter and the mass of ions, wherein ions scattered from said surface at a predetermined angle are accepted and a portion of accepted ions are passed therethrough,
   establishing a time varying predetermined condition definitive of a given kinetic parameter within the first of said analyzer means through which said accepted ions are directed to allow only ions having a said kinetic parameter to pass therethrough,
   establishing another predetermined condition definitive of a given mass within the second of said analyzer means through which said accepted ions are directed to allow only ions having a said given mass therethrough such that the mass and kinetic parameter of the detected ions are both known, thereby enabling the direct inference of the mass of surface atoms from which the ions are scattered, and
   detecting the scattered ions passing through both of said analyzer means that have a given kinetic parameter and a given mass to generate a signal characteristic of surface atoms having a given mass.

2. A method according to claim 1, further comprising establishing a predetermined condition at a region within one of said analyzer means to allow only ions having the same mass as the primary ions to pass therethrough.

3. In an apparatus for analyzing the surface of a material comprising
   means for generating a primary ion beam,
   means for directing said beam along a preselected path to impinge upon and be scattered from a surface of the material to be analyzed,
   means for transmitting ions indicative of surface atoms having a given mass, and means for receiving the transmitted ions and converting the received ions into an electronic signal characteristic of said surface atoms, the improvement wherein said transmitting means comprises two independent analyzer means positioned in tanden adjacent to said surface for determining the characteristics consisting of the mass and the kinetic parameters energy, momentum and velocity of ions, wherein ions scattered from said surface at a predetermined angle are accepted and a portion of said accepted ions are passed therethrough, means for establishing a time varying predetermined condition definitive of a given kinetic parameter within the first of said analyzer means through which said accepted ions are directed to allow only ions having a first said given characteristic to pass therethrough, means for establishing another predetermined condition definitive of a given mass within the second of said analyzer means through which said accepted ions are directed to allow only ions having a said second given characteristic to pass therethrough such that the mass and kinetic parameters of the detected ions are both known, thereby enabling the direct inference of the mass of surface atoms from which the ions are scattered, and means for detecting the scattered ions passing through both of said analyzer means that have a given set of said first and second given characteristics to generate a signal characteristic of surface atoms having a given mass.

4. An apparatus according to claim 3, wherein the first analyzer means is an energy analyzer.

5. An apparatus according to claim 1, further comprising means positioned between the first and mass analyzers for collecting ions passed through said first analyzer and for optimizing the passage thereof into said mass analyzer.

6. An apparatus according to claim 5, wherein said collecting and optimizing means comprises a lens and wherein said mass analyzer comprises a quadrupole mass filter.

7. An apparatus according to claim 6, wherein said lens is a retarding lens and said quadrupole mass filter is biased to accept the thus retarded ions, thereby maximizing the mass selectivity of said quadrupole mass filter.

8. An apparatus according to claim 1, wherein said energy analyzer means comprises an electrostatic first filter having an entrance aperture positioned to receive ions scattered at a predetermined angle and having an exit aperture for passing ions having a given energy loss, and said mass analyzer comprises a quadrupole mass filter having an entrance end positioned adjacent said exit aperture of said energy filter to receive said passed ions.

9. In an apparatus for analyzing the outer surface of a material comprising means for generating a low energy ion beam substantially homogeneous in mass and energy, means for directing said beam along a preselected path to impinge onto a surface of the material to be analyzed, means for measuring the loss of energy of ions scattered at a predetermined angle relative to impinging ion beam, and means for producing an energy spectrum corresponding to a plot of the magnitude of scattered ions having a given energy loss as a function of the ratio of said energy after scattering to the initial energy of the incident beam, the improvement wherein said energy loss measuring means comprises energy analyzer means having an entrance portion positioned adjacent said surface for accepting ions emanating therefrom substantially at said predetermined angle, means for applying a time varying electrostatic field within said energy analyzer means through which said accepted ions are directed whereby a given electrostatic field allows only such ions as have a given energy to pass through an exit portion of said energy analyzer, mass analyzer means positioned adjacent said exit portion for receiving said passed ions and for deflecting said passed ions such that only ions having a given mass are deflected through an exit portion, and means for detecting the ions at the exit portion of the mass analyzer to generate a signal corresponding to the instantaneous concentration of scattered ions having a given energy loss and a given mass such that the independent determination of the energy loss and mass of the detected ions enables the direct inference of the mass of surface atoms from which the ions are scattered.

10. In an apparatus for analyzing the surface of a material comprising means for generating a primary ion beam, means for directing said beam along a preselected path to impinge upon and be scattered from a surface of the material to be analyzed, means for transmitting ions indicative of surface atoms having a given mass, and means for receiving the transmitted ions and converting the received ions into an electronic signal characteristic of said surface atoms, the improvement wherein said receiving and converting means comprises an analyzer means positioned proximate to said surface for accepting ions scattered from said surface at a given angle and for passing ions having a preselected value of one of the kinetic parameters energy momentum or velocity, and a quadrupole mass filter positioned proximate an exit portion of said analyzer means for accepting said passed ions and for further passing only such accepted ions as have a given mass and a lens positioned between the analyzer means and the quadrupole mass filter for collecting ions passed through the analyzer means and for optimizing the passage thereof into the quadrupole mass filter, means for establishing a time varying predetermined condition within said analyzer means through which said accepted ions are directed to allow passage therethrough of only such ions as have a said preselected value, means for establishing another predetermined condition within said quadrupole mass filter to allow only ions having said given mass to pass therethrough, and means for detecting the scattered ions passing through both said analyzer means and said mass filter to generate a signal characteristic of surface atoms having a given mass.

* * * * *

UNITED STATES PATENT AND TRADEMARK OFFICE
CERTIFICATE OF CORRECTION

PATENT NO. : 4,058,724
DATED : November 15, 1977
INVENTOR(S) : James T. McKinney and Robert F. Goff It is certified that error appears in the above-identified patent and that said Letters Patent are hereby corrected as shown below:

Column 1, lines 58-59, delete "or velocity analyzers (time-of-flight spectrometers)".

Column 2, line 21, change "parameter" to -- parameters --.

Column 3, line 17, change "rations" to -- ratios --.

Column 9, line 49, change "energy" to -- first -- and change "first" to -- energy --.

Signed and Sealed this

Second Day of May 1978

[SEAL]

Attest:

RUTH C. MASON
Attesting Officer

LUTRELLE F. PARKER
Acting Commissioner of Patents and Trademarks